United States Patent
Lesnik Oberstein et al.

(10) Patent No.: US 9,062,311 B2
(45) Date of Patent: Jun. 23, 2015

(54) MEANS AND METHODS FOR MODULATING NOTCH3 PROTEIN EXPRESSION AND/OR THE CODING REGION OF NOTCH3; COMPOSITIONS AND USE THEREOF IN THE TREATMENT OF CADASIL

(75) Inventors: Saskia Anne-Marie Jenny Lesnik Oberstein, Oegstgeest (NL); Garrit-Jan Boudewijn van Ommen, Amsterdam (NL); Adriana Marie Rus, Hoofddorp (NL); Johannes Gregorius Dauwerse, Delft (NL)

(73) Assignee: ACADEMISCH ZIEKENHUIS LEIDEN H.O.D.N. LUMC, Leiden (NL)

( * ) Notice: Subject to any disclaimer, the term of this patent is extended or adjusted under 35 U.S.C. 154(b) by 31 days.

(21) Appl. No.: 13/145,873

(22) PCT Filed: Jan. 26, 2010

(86) PCT No.: PCT/NL2010/050036
§ 371 (c)(1),
(2), (4) Date: Sep. 7, 2011

(87) PCT Pub. No.: WO2010/085151
PCT Pub. Date: Jul. 29, 2010

(65) Prior Publication Data
US 2011/0318787 A1    Dec. 29, 2011

(30) Foreign Application Priority Data

Jan. 26, 2009   (EP) .................................... 09151326

(51) Int. Cl.
*C12Q 1/68* (2006.01)
*C12N 15/113* (2010.01)
*C07K 14/705* (2006.01)

(52) U.S. Cl.
CPC ....... *C12N 15/1138* (2013.01); *C07K 14/70567* (2013.01); *C12N 2310/11* (2013.01); *C12N 2320/33* (2013.01)

(58) Field of Classification Search
None
See application file for complete search history.

(56) References Cited

U.S. PATENT DOCUMENTS

2003/0186290 A1* 10/2003 Tournier-Lasserve et al. ... 435/6
2004/0102390 A1*  5/2004 Freier et al. ..................... 514/44

OTHER PUBLICATIONS

Kalimo et al. (Future Neurol 2008, 3:683-704).*
Saiki S, et al., Varicose Veins Associated With Cadasil Result . . . , Neurology Jul. 25, 2006, vol. 67, No. 2, pp. 337-339, XP002526569.
Federico, et al., The Spectrum of Mutations for Cadasil Diagnosis, Neurological Sciences; Official Journal of the Italian Neurological Society, vol. 26, No. 2, Jun. 1, 2005, pp. 117-124, XP019361567.
Van Ommen Gert-Jan, et al., The Therapeutic Potential of Antisense-Mediated . . . , Current Opinion in Molecular Therapeutics, current Drugs, London, GB, vol. 10, No. 2, Apr. 1, 2008, pp. 140-149, XP009107079.
P. Jeanteur, Regulation of Alternative Splicing (2003).

* cited by examiner

*Primary Examiner* — Kimberly Chong
(74) *Attorney, Agent, or Firm* — Lucas & Mercanti, LLP (57) ABSTRACT

The invention among other provides means and methods for modulating NOTCH3 expression and/or protein coding domain. In one aspect the invention provides a method for at least reducing an elevated level of NOTCH3 protein in a NOTCH3 expressing cell or the immediate vicinity thereof said method comprising providing said cell with an anti-sense oligonucleotide specific for NOTCH3 m RNA or pre-m RNA thereby decreasing production of said NOTCH3 protein or thereby altering the protein coding region in said NOTCH3 m RNA or pre-m RNA.

6 Claims, 2 Drawing Sheets

MEANS AND METHODS FOR MODULATING NOTCH3 PROTEIN EXPRESSION AND/OR THE CODING REGION OF NOTCH3; COMPOSITIONS AND USE THEREOF IN THE TREATMENT OF CADASIL

CROSS-REFERENCE TO RELATED APPLICATIONS

This application is a 371 of PCT/NL2010/050036 filed Jan. 26, 2010, which claims the benefit of European Patent Application No. 09151326.7 filed Jan. 26, 2009, the contents of each of which are incorporated herein by reference.

FIELD OF THE INVENTION

The invention relates to the fields of biology and medicine. In particular the invention relates to EGF-repeat containing proteins such as NOTCH3, mutations therein and methods to overcome a mutation.

BACKGROUND OF THE INVENTION

Cerebral autosomal dominant arteriopathy with subcortical infarcts and leukoencephalopathy (CADASIL) is an adult-onset (14-86 years), dominantly inherited disorder caused by NOTCH3 mutations and is characterized by recurrent subcortical infarctions, dementia, and less frequently, migraine and psychiatric symptoms. NOTCH3 has 33 exons, and CADASIL-associated NOTCH3 mutations resulting in an uneven number of cysteine residues within a given extracellular epidermal growth factor (EGF)-like repeat (EGFL-repeat) domain with a strong clustering in exon 3 to 6 encoding the first five EGFL-repeats. The typical MRI features in CADASIL include multi-focal lacunar infarcts and diffuse T2-weighted hyperintensity of cerebral white matter with involvement of the anterior temporal lobe. Electronmicroscopy (EM) shows the presence of granular osmiophilic material (GOM) in the media of arterioles, in close vicinity to the basement membrane of the smooth muscle cells, and is pathognomonic for CADASIL.

The identity of this granular osmiophilic material is only partly known, but has been shown to contain mutated NOTCH3 protein.

SUMMARY OF THE INVENTION

The CADASIL phenotype of the present invention is caused by mutations in the NOTCH3 gene. This gene is expressed in vascular smooth muscle cells (VSMC) and pericytes and encodes the NOTCH3 protein, which is a transmembrane receptor with a cell-signalling function. In patients with CADASIL there is accumulation of the NOTCH3 ectodomain on the surface of degenerating VSMC as well as accumulation of granular osmiophilic deposits (GOM) in the vicinity of VSMC. The VSMC degeneration leads to impaired vascular reactivity and decreased cerebral blood flow, and thus to recurring cerebral infarctions and progressive cognitive decline. Although CADASIL affects arteries throughout the body, for unknown reasons the disease manifests itself particularly in the central nervous system.

Although the pathogenesis of the disease at the molecular and cellular level is still poorly understood, it has been shown that there is misfolding of the protein due to the characteristic mutations resulting in an unequal number of cysteine residues in one of the protein's 34 EGFL-repeats (EGFL-repeat). Typically, each EGFL-repeat contains 6 cysteine residues. Mutations in NOTCH3 leading to an uneven number of cysteine residues (usually either 5 or 7 residues) causes CADASIL. Several studies have shown that, for almost all mutations studied, NOTCH3 signalling is not changed in the presence of mutant NOTCH3. It is speculated that the core of the problem is a toxic effect of mutated NOTCH3 and, or GOM accumulation on VSMC. NOTCH3 and GOM accumulation in VSMC is pathognomonic for CADASIL and is also observed in NOTCH3 transgenic mouse and cell models.

In the present invention it was found that re-establishing an equal number of cysteine residues in a given mutated EGFL-repeat of the NOTCH3 protein by generating a shorter mRNA product, and/or reducing the expression of mutant NOTCH3 mRNA reduces and/or delays the accumulation of the NOTCH3 ectodomain on the surface of VSMC. NOTCH3 mRNA with an equal number of cysteines in all EGFL-repeats and/or reduction of mutant NOTCH3 mRNA expression also reduces and/or delays the degeneration of VSMC in subjects suffering or at risk of suffering from CADASIL. In the present invention it was found that re-establishing an equal number of cysteines in a given mutated EGFL-repeat and/or a reduction in NOTCH3 mRNA expression, reduces the toxic effect of the unpaired cysteine residue created by the disease-causing mutation. Most of the mutations in the NOTCH3 gene are present in exon 4. It was found that the exclusion of exon 4 and exon 5 from the mRNA generates a coding region wherein all of the remaining EGFL-repeats have an even number of cysteines.

DETAILED DESCRIPTION OF THE INVENTION

The invention therefore provides a method for producing an mRNA encoding a NOTCH3 protein having EGFL-repeats with even numbers of cysteines from a pre-mRNA encoding a mutant NOTCH3 protein having an EGFL-repeat with an uneven number of cysteines. This is achieved by providing a cell expressing said pre-mRNA with an antisense oligonucleotide that is complementary to and hybridizes with said pre-mRNA and that thereby induces the exclusion of exon 4 and exon 5 from mRNA produced from said pre-mRNA. Preferably, said EGFL-repeat with an uneven number of cysteines is encoded by exon 4 and/or exon 5. The invention is useful for any mutation in exon 4 or 5 that results in an uneven number of cysteines. The list of mutations is growing continuously with new patients being identified and sequenced. Documented mutations for which the invention is useful are those in which said pre-mRNA encodes a NOTCH3 protein with a mutation Arg133Cys, Cys134Trp, Arg141Cys, Cys144Phe, Arg153Cys, Cys162Trp, Arg182Cys, Tyr189Cys, Arg207Cys, Cys224Tyr, Arg207Cys, Cys224Tyr or a combination thereof.

The invention further provides a method for reducing the amount of mutant NOTCH3 protein produced by a cell that expresses a pre-mRNA encoding said mutant NOTCH3 protein, wherein said mutant NOTCH3 protein comprises an EGFL-repeat with an uneven number of cysteines. Said method comprises providing said cell with an antisense oligonucleotide that is complementary to and capable of hybridizing to the nucleotide sequence that encodes the mutation that is the cause of the uneven number of cysteines in said EGFL-repeat in exon 4 and/or exon 5 of the NOTCH3 gene. In a preferred embodiment said method comprises providing said cell with an antisense oligonucleotide that is complementary to and capable of hybridizing to the nucleotide sequence that encodes the mutation that is the cause of the uneven number of cysteines in said EGFL-repeat in exon 5 of the NOTCH3 gene. In another preferred embodiment said method comprises providing said cell with an antisense oligonucleotide that is complementary to and capable of specifically hybridizing to the pre-mRNA encoding the mutant NOTCH3 protein. The specific hybridisation to the pre-mRNA encoding the mutant NOTCH3 protein is preferably achieved using an oligonucleotide that is specific for CADASIL causing mutation. The CADASIL causing mutation is often in exon 4 or exon 5, however, other CADASIL causing mutations in a NOTCH3 pre-mRNA are also within the scope of the present invention. In other words the oligonucleotide is complementary to and overlaps with mutation causing CADASIL. In this respect the oligonucleotide can be specific for any one of exons 2-32, preferably the oligonucleotide is specific for any one of exons 2-23. Preferably the oligonucleotide is specific for the nucleotide sequence that encodes the mutation that is the cause of the uneven number of cysteines in said EGFL-repeat in exon 4 and/or exon 5 of the NOTCH3. The gene encoding NOTCH3 protein is polymorphic. Various NOTCH3 alleles are identified that encode a NOTCH3 protein with a normal function. In a cell that is heterozygous for a mutant CADASIL causing allele, the mutant allele can differ from the normal allele in that cell not only in the presence of the disease causing mutation but also in the presence of a different sequence in a polymorphic site. This polymorphic site thus also characterises the mutant allele in this heterozygote.

The present invention thus in another preferred embodiment provides a method for reducing the amount of mutant NOTCH3 protein produced by a cell that expresses a first pre-mRNA encoding said mutant NOTCH3 protein, and a second pre-mRNA encoding a normal NOTCH3 protein, wherein said first and said second pre-mRNA differ from each other in the presence of the CADASIL causing mutation in the mutant allele and in the presence of a different sequence in a polymorphic site different from site mutation, and wherein said method for reducing the amount of mutant NOTCH3 protein comprises providing said cell with an anti-sense oligonucleotide that is complementary to and capable of specifically hybridizing to the sequence of the polymorphic site present on the pre-mRNA encoding the mutant NOTCH3 protein. Further provided is a method for reducing the amount of mutant NOTCH3 protein produced by a cell that expresses a first pre-mRNA encoding said mutant NOTCH3 protein, and a second pre-mRNA encoding a normal NOTCH3 protein, wherein said first and said second pre-mRNA differ from each other in the presence of a CADASIL causing mutation in the mutant allele and in the presence of a different sequence in a polymorphic site different from the site of said mutation, said method comprising providing said cell with an antisense oligonucleotide that is complementary to and capable of hybridizing to the sequence of the polymorphic site present on the pre-mRNA encoding the mutant NOTCH3 protein.

In a preferred embodiment said oligonucleotide is specific for the sequence of a polymorphic site in any one of exons 2-32. In a preferred embodiment the amount of pre-mRNA encoding the CADASIL causing mutant is reduced by means of exon skipping. Preferably by means of a exon skip that introduces a frameshift in the protein coding domain of the mutant allele. Preferably said frameshift introduces a premature stop of the protein. In this embodiment it is preferred that the oligonucleotide is specific for an exon of exons 2, 3, 4, 5, 13, 14, 17, 18, 19, 20, 21, 23, 24, 26, 27, 28, 29, 30, 31, and 32.

In another preferred embodiment, the oligonucleotide is specific for an exon of exons 2-23, preferably for an exon of exons 2, 3, 4, 5, 13, 14, 17, 18, 19, 20, 21 and 23. In another preferred embodiment, the oligonucleotide is specific for an exon of exons 2-10. In a particularly preferred embodiment said oligonucleotide is specific for an exon of exons 2-5. In a preferred embodiment said anti-sense oligonucleotide is specific for a CADASIL causing mutation or polymorphic site in any one of the exons identified herein above. In a particularly preferred embodiment said anti-sense oligonucleotide is specific for a CADASIL causing mutation in exon 2, 3, 4 or 5, and/or specific for a polymorphic site in exon 2, 3, 4 or 5.

In a preferred aspect of the embodiments said antisense oligonucleotide is a chemically modified antisense nucleotides (including but not limited to 2'-O-methyl RNA with or without a phosphorothioate backbone, locked nucleic acids (LNA), peptide nucleic acids (PNA), phosphorodiamidate morpholino oligomers (PMO), 2'-O-methoxyethyl RNA with or without a phosphorothioate backbone and chimeric oliogos consisting of a combination of one or more different chemically modified nucleotides). In another preferred embodiment said oligonucleotide is an SiRNA, or an miRNA The invention further provides a method for at least reducing the level of NOTCH3 protein in a NOTCH3 expressing cell or the immediate vicinity thereof. Said method comprises providing said cell with an anti-sense oligonucleotide specific for NOTCH3 mRNA or pre-mRNA thereby decreasing production of said NOTCH3 protein or thereby altering the protein coding region in said NOTCH3 mRNA or pre-mRNA. In the latter embodiment it is preferred that the anti-sense oligonucleotide effects an alteration of the splicing of the NOTCH3 pre-mRNA resulting in an alternatively spliced mRNA. Alternative splicing induced by anti-sense oligonucleotides is typically targeted toward the exclusion of a targeted exon. However, so-called exon inclusion is also possible. The alternatively spliced mRNA preferably encodes an at least partially functional NOTCH3 protein. Typically, though not necessarily, an exon that is normally present in the mRNA is skipped. The specific skipping of an exon in pre-mRNA that encodes the mutant NOTCH3 protein is beneficial in two ways. In a preferred embodiment said cell comprises a NOTCH3 encoding gene with a mutation as depicted in table 1, when compared to a NOTCH3 encoding gene of a healthy individual. Skipping of exon 4 and exon 5 together results in an exon 3-6 joining that is in frame and encodes a NOTCH3 protein in which the remaining EGFL repeats all have an even number of cysteine residues. Thus in a preferred embodiment of the invention both exon 4 and exon 5 are skipped. Specific skipping of only a mutated exon 4 or only a mutated exon 5 results in joined exons 3-5 for the exon 4 skip and joined exons 4-6 for the exon 5 skip. These latter joinings result in an out of frame protein coding domain whereby a premature stop is introduced resulting in a truncated non-functional protein. This skipping results in a decrease of the production of the originally mutant protein and thereby putatively alleviates the symptoms of the CADASIL patient.

In a preferred embodiment the cell to be treated expresses a NOTCH3 protein comprising an EGFL-repeat with an uneven number of cysteine residues. Said mutation is preferably a mutation as listed in table 1. Said mutation is preferably Arg141Cys; Arg153Cys; Arg182Cys and Arg207Cys of table 1.

Numerous different NOTCH3 mutations have been identified within affected families. Studies in unrelated individuals reveal strong clustering of the mutations, upto 70% of them occurring in exons 4 and 5. It has also been found that the mutation can occur spontaneously in individuals, an observation which raises important issues about diagnostic testing for NOTCH3 mutations in the wider stroke population. Almost all cases described to date are in individuals heterozygous for NOTCH3 mutations, although patients with homozygous mutations have been described.

Mutations are characteristic in that they lead to either loss or gain of a cysteine residue in one of the proteins EGFL-repeats. Such mutations alter the conformation of the protein, leading to accumulation of NOTCH3 protein on the vascular smooth muscle cell membrane, which is probably toxic for said cell.

The Notch3 gene encodes a transmembrane receptor containing several tandemly repeated copies of an epidermal growth factor-like repeat (EGFL-repeat) and plays a role in transducing signals between neighbouring cells. Notch signalling is a highly conserved pathway involved in cell signalling and fate during embryonic development, including many aspects of vascular development, but the role of Notch3 in normal adult vascular smooth muscle cell physiology is largely unknown. Recent work suggests that Notch3 is involved in vascular injury and is a determinant of vascular smooth muscle cell survival.

The CADASIL phenotype of the present invention is, as mentioned herein above, associated with the expression of a mutant NOTCH3 protein. Pathogenesis in humans is mainly associated with the expression of the mutant protein in vascular smooth muscle cells (VSMC). It is therefore preferred that expression in this type of cell is reduced and/or modified. In a particularly preferred embodiment of the present invention the mutant protein that is associated with CADASIL is modified to allow the production of a modified mutant CADASIL protein having EGFL-repeats with an even number of cysteines. In other words, it is preferred that the CADASIL mutation of NOTCH3 that result in the presence of an EGFL-repeat with an uneven number of cysteines is counteracted by the modification of the present invention, resulting in a new NOTCH3 mutant (restoring NOTCH3 mutant) having only EGFL-repeats with even numbers of cysteines. Without being bound by theory it is believed that restoring the even number produces an at least partially functional NOTCH3 mutant protein. It is further believed that the restoring NOTCH3 mutant does not accumulate or at least accumulates to a lesser extent than the NOTCH3 mutants resulting in the CADASIL phenotype. Production of the restoring NOTCH3 mutant further results in a decrease of the amount of GOM. It further results in reduced VSMC degeneration, and ultimately to a reduction in the risk for ischemic stroke and dementia in the individual suffering from or at risk of suffering from CADASIL.

The restoring NOTCH3 mutant is preferably produced by allowing exon-skipping to occur. Exon-skipping results in the exclusion of an exon from NOTCH3 encoding mRNA. Exon-skipping is typically induced by an oligonucleotide that is directed toward the splice sites flanking the exon or by an exon-internal oligonucleotide. NOTCH3 contains 33 exons of which exons 1-33 encode part of the protein. Exon 1 and exon 33 contain respectively the start and stop codon. Exons 2 to 23 encode the protein's EGFL-repeats. In a preferred embodiment said anti-sense oligonucleotide induces skipping of a NOTCH3 protein EGFL-coding exon.

Skipping of exons 4 and 5 results in an in frame mutant NOTCH3 protein. Particularly preferred is the skipping of exon 4 and exon 5 as these exons harbour ~70% of all currently identified CADASIL mutations. Skipping of these exons leads to an in-frame product with, on the protein level, the complete loss of EGFL-repeats 3, 4 and 5, whereas EGFL-repeats 2 and 6 are predicted to form a functional fusion EGFL-repeat with exactly 6 cysteine residues. The skip will be induced by creating antisense oligonucleotides (AONs) targeted to internal exon 4 and 5 sequences. In addition to exon-specific AONs, preferably mutation-specific AONs will be used. This technique of using AON's to skip EGFL-repeats in order to skip a mutation in a given EGFL-repeat, could also be applied to other cell-surface receptors with a repetitive sequence of EGFL-repeats, such as the DSL-ligands of NOTCH3: Delta-likel, 3 and 4.

The skipping of exon 4 is preferred for mutations Arg141Cys; Arg153Cys; Arg182Cys and Arg207Cys of table 1. The skipping of exon 5 is preferred for mutations Cys233Trp and Tyr258Cys of table 1. The resulting restoring NOTCH3 mutant proteins have EGFL-repeats with an even number of cysteines.

The anti-sense oligonucleotide is preferably complementary to a consecutive part of between 13 and 50 nucleotides of said NOTCH3 pre-mRNA. Preferably said anti-sense oligonucleotide is complementary to a consecutive part of between 16 and 50 nucleotides of said NOTCH3 pre-mRNA. In a preferred embodiment said anti-sense oligonucleotide comprises between 15-40 nucleotides specific for said NOTCH3 mRNA or pre-mRNA. The number of bases that are sufficient and/or optimal for inducing exon skipping is dependent on several factors. Some types of oligonucleotide usually require somewhat longer oligonucleotides for instance, morpholinos typically have between about 25-30 consecutive bases whereas 2'O-methyl phosphorothioate oligonucleotides typically have their activity optimum between about 20-25 bases. For the present invention it is therefore preferred that said anti-sense oligonucleotide is complementary to a consecutive part of between about 15 and 35 nucleotides. More preferably said oligonucleotide is complementary to a consecutive part of between about 20 and 30 nucleotides.

Different types of nucleic acid may be used to generate the oligonucleotide. Preferably, the oligonucleotide comprises RNA, as RNA/RNA hybrids are very stable. Since one of the aims of the exon skipping technique is to direct splicing in subjects it is preferred that the oligonucleotide RNA comprises a modification providing the RNA with an additional property. Some types of anti-sense oligonucleotides render the target (pre-mRNA) sensitive to nucleases such as RNAseH. Oligonucleotides that render the duplex formed by the antisense oligonucleotide and the target pre-mRNA sensitive to RNAseH degradation are preferred for embodiments wherein the amount of mutant NOTCH3 protein is to be reduced by degradation of the (pre-)mRNA encoding the mutant. When only exon-skipping is intended, it is preferred that the anti-sense oligonucleotide does not have this property and thus comprises a modification that renders the duplex formed by the antisense oligonucleotide and the target pre-mRNA resistant to RNAseH. Various oligonucleotides and modifications and variants thereof do not promote the nuclease degradation of the target (pre-)mRNA. Examples of such types of oligonucleotides are 2'-O-methyl phosphorothioate oligonucleotides and morpholinos. Other features that may be added to or enhanced in said anti-sense oligonucleotide are increased stability (for instance in a bodily fluid), increased or decreased flexibility, reduced toxicity, increased intracellular transport, tissue-specificity, etc. Preferably said modification comprises a 2'-O-methyl-phosphorothioate oligoribonucleotide modification. Preferably said modification comprises a 2'-O-methyl-phosphorothioate oligodeoxyribonucleotide modification. In one embodiment the invention provides a hybrid oligonucleotide comprising an oligonucleotide comprising a 2'-O-methyl-phosphorothioate oligo(deoxy)ribonucleotide modification and locked nucleic acid. This particular combination comprises better sequence specificity compared to an equivalent consisting of locked nucleic acid, and comprises improved effectivity when compared with an oligonucleotide consisting of 2'-O-methylphosphorothioate oligo(deoxy)ribonucleotide modification.

With the advent of nucleic acid mimicking technology it has become possible to generate molecules that have a similar, preferably the same hybridisation characteristics in kind not necessarily in amount as nucleic acid itself. Such equivalents are of course also part of the invention. Examples of such mimic equivalents are peptide nucleic acid, locked nucleic acid and/or a morpholino phosphorodiamidate. Suitable but non-limiting examples of equivalents of oligonucleotides of the invention can be found in (Wahlestedt, C. et al. Potent and non-toxic antisense oligonucleotides containing locked nucleic acids. Proc Natl Acad Sci USA 97, 5633-8. (2000). Elayadi, A. N. & Corey, D. R. Application of PNA and LNA oligomers to chemotherapy. Curr Opin Investig Drugs 2, 558-61. (2001). Larsen, H. J., Bentin, T. & Nielsen, P. E. Antisense properties of peptide nucleic acid. Biochim Biophys Acta 1489, 159-66. (1999). Braasch, D. A. & Corey, D. R. Novel antisense and peptide nucleic acid strategies for controlling gene expression. Biochemistry 41, 4503-10. (2002). Summerton, J. & Weller, D. Morpholino antisense oligomers: design, preparation, and properties. Antisense Nucleic Acid Drug Dev 7, 187-95. (1997)). Hybrids between one or more of the equivalents among each other and/or together with nucleic acid are of course also part of the invention. In a preferred embodiment an equivalent comprises locked nucleic acid, as locked nucleic acid displays a higher target affinity and reduced toxicity and therefore shows a higher efficiency of exon skipping. An anti-sense oligonucleotide of the invention is preferably complementary in a consecutive stretch of nucleotides. However, typically one or two mismatches are tolerated without reducing the efficiency of skipping or reduction of target RNA too much. Oligonucleotides having such one or two mismatches can thus also be used in the present invention. Presently analogues of bases are available that show the same type of base pairing as their natural counterpart. Such analogues may therefore also be included in the oligonucleotide of the present invention. Some base analogues are available that pair differently than the natural counterpart. For instance inosine does not pair with the opposing base. Such base analogues can also be included in the oligonucleotide of the present invention. Non-base pairing analogues typically reduce the hybridization strength of the oligonucleotide. For this reason it is preferred that the oligonucleotide comprises additional nucleotides to compensate for this reduction. An oligonucleotide of the invention typically does not have to overlap with a splice donor or splice acceptor of the exon.

An oligonucleotide of the invention may be provided to a cell as such or in the context of a nucleic acid delivery vehicle. Oligonucleotides can be transfected into the cell using a transfection agent such as a liposome or PEI.

Alternatively, the oligonucleotide is introduced into the cell with a viral, or virus-based gene delivery vehicle. The oligonucleotide can also be encoded by an expression cassette provided to said cell. Typically, the oligonucleotide is encoded by an expression cassette in said viral or virus-based gene delivery vehicle. The oligonucleotide may then be contained with a transcript comprising said oligonucleotide. Thus preferably said expression cassette encodes an RNA comprising said anti-sense oligonucleotide. Thus the gene delivery vehicle can contain an expression cassette. An expression cassette contains the sequence to be expressed together with all sequences necessary for expression of the sequence for instance a suitable promoter and transcription termination sequence. The expression vector is preferably introduced into the cell via a gene delivery vehicle. A preferred delivery vehicle is a viral vector such as an adenoviral vector and more preferably an adeno-associated virus vector. The invention thus also provides such expression vectors and delivery vehicles. It is within the skill of the artisan to design suitable transcripts. Preferred for the invention are PolIII driven transcripts. Preferably in the form of a fusion transcript with an U1 or U7 transcript. Such fusions may be generated as described in Gorman L, Suter D, Emerick V, et al. Stable alteration of pre mRNA splicing patterns by modified U7 small nuclear RNAs. Proc Natl Acad Sci USA 1998; 95:4929 4934 and Suter D, Tomasini R, Reber U, et al. Double target antisense U7 snRNAs promote efficient skipping of an aberrant exon in three human beta thalassemic mutations. Hum Mol Genet 1999; 8:2415 2423.

The invention further provides the use of an anti-sense oligonucleotide for a NOTCH3 mRNA or pre-mRNA, an expression cassette and/or a gene delivery vehicle of the invention for the treatment of Cerebral Autosomal Dominant Arteriopathy with Subcortical Infarcts and Leukoencephalopathy (CADASIL). Also provided is the use of an anti-sense oligonucleotide for a NOTCH3 mRNA or pre-mRNA, an expression cassette and/or a gene delivery vehicle of the invention for the preparation of a medicament for the treatment of CADASIL. The invention further provides the use of an antisense oligonucleotide complementary to and capable of specifically hybridizing to a specific sequence of a polymorphic site on a pre-mRNA encoding a NOTCH3 protein, for reducing the amount of mutant NOTCH3 protein in a cell, wherein said cell contains a first pre-mRNA encoding said mutant protein and that contains said specific sequence of said polymorphic site and said cell contains a second pre-mRNA encoding a normal NOTCH3 protein and that contains a different sequence of said polymorphic site.

The invention further provides a method for decreasing the level of VSMC degeneration and/or granular osmiophilic deposits in an individual suffering from CADASIL or at risk of suffering therefrom, comprising providing said individual with an oligonucleotide for a NOTCH3 mRNA or pre-mRNA according to the invention, an expression cassette or a gene delivery vehicle of the invention.

The invention further provides a NOTCH3 encoding nucleic acid encoding a NOTCH3 protein having less than 34 EGFL-repeats. Further provided is a NOTCH3 encoding nucleic acid encoding a NOTCH3 protein having 22 or more EGFL-repeats. Preferably said nucleic acid encoding a NOTCH3 protein has 30 EGFL repeats. Further provided is a NOTCH3 encoding nucleic acid encoding a NOTCH3 protein that is missing the NOTCH3 coding sequence of exons 4 and 5. A NOTCH3 encoding nucleic acid encoding a NOTCH3 mutant according to the invention preferably comprises EGFL-repeats having an even number of cysteines. Preferably essentially all EGFL-repeats present in said mutant NOTCH3 protein have an even number of cysteines. Further provided is an isolated and/or recombinant NOTCH3 protein comprising an amino acid sequence encoded by a nucleic acid as detailed in this paragraph.

Further provided is an antisense oligonucleotide that is specific for a mutation in a NOTCH3 gene, whereby said mutation results in a NOTCH3 protein comprising an uneven number of cysteines in an EGFL repeat. As CADASIL is a dominantly inherited disease, most individuals suffering from CADASIL or at risk of suffering therefrom are heterozygous for the affected allele. Thus one allele produces the normal NOTCH3 protein. An oligonucleotide of the invention is therefore preferably specific for the mutant allele. In this way only the affected (pre-)mRNA is targeted. Preferably said anti-sense oligonucleotide is specific for a common recurrent mutation in the NOTCH3 gene. Preferably said antisense oligonucleotide is specific for exon 4 or exon 5. In a preferred embodiment said antisense oligonucleotide is specific for a CADASIL mutation of table 1, preferably the Arg207Cys, the Arg141Cys, the Arg182Cys or the Arg153Cys mutation of a NOTCH3 gene. In another preferred embodiment the invention provides an antisense oligonucleotide specific for a sequence in a polymorphic site in any one of exons 2-32. Preferably said antisense oligonucleotide is an oligonucleotide that causes skipping of an exon of NOTCH3. The oligonucleotide is preferably specific for an exon of exons 2, 3, 4, 5, 13, 14, 17, 18, 19, 20, 21, 23, 24, 26, 27, 28, 29, 30, 31, and 32.

In another preferred embodiment, the oligonucleotide is specific for an exon of exons 2-23, preferably for an exon of exons 2, 3, 4, 5, 13, 14, 17, 18, 19, 20, 21 and 23. In another preferred embodiment, the oligonucleotide is specific for an exon of exons 2-10. In a particularly preferred embodiment said oligonucleotide is specific for an exon of exons 2-5. In a preferred embodiment said anti-sense oligonucleotide is specific for a CADASIL causing mutation or sequence in a polymorphic site in any one of the exons identified herein above. In a particularly preferred embodiment said anti-sense oligonucleotide is specific for a CADASIL causing mutation in exon 2, 3, 4 or 5, and/or specific for a sequence in a polymorphic site in exon 2, 3, 4 or 5.

The invention further provides a method for decreasing the level of VSMC degeneration and/or granular osmiophilic deposits in an individual suffering from CADASIL or at risk of suffering therefrom, comprising providing said individual with a nucleic acid for decreasing the amount of NOTCH3 protein in a VMSC or to modify a mutant NOTCH3 protein in a VMSC of said individual. Various methods are available in the art to reduce the amount of a specific mRNA or the translation thereof. Examples include but are not limited to, siRNA, miRNA, anti-sense RNA and DNA molecules and analogues thereof. A preferred anti-sense oligonucleotide is a morpholine with the same hybridisation characteristics in kind not necessarily in amount as unmodified anti-sense oligonucleotide. In the present invention it is preferred that these are specific for the NOTCH3 mutation that is associated with CADASIL. In another preferred embodiment, said nucleic acid for decreasing the amount of NOTCH3 protein in a VMSC encodes an antibody specific for NOTCH3, or a fragment or analogue thereof. Preferably said antibody is specific for the NOTCH3 protein mutant that is associated with CADASIL.

It is known that a single mismatch with the target sequence can (almost) completely abolishes the AON efficacy when this mismatch is located in the middle of the target sequence. The advantage of mutation-specific AONs is that they will not interfere significantly with transcription of the wild-type allele. The disadvantage is that multiple AONs would have to be designed to target the diverse NOTCH3 mutations. The benefit of exon-specific AONs is that targeted single- or multi-exon skipping of mutation hotspot exons 4 or 5 can benefit up to 70% of mutations in CADASIL patients. A draw-back of this approach is that the wild type allele will also be targeted and modified. However, as in the present invention the modified protein will retain normal function, this should not pose a problem. In a preferred embodiment however undesired targeting of the wild-type allele in exon-specific skipping could be circumvented using SNP-specific AONs. The Notch3 coding region exhibits polymorphism. Individuals can have two different polymorphic alleles and these can be specifically targeted in CADASIL patients to target the mutated allele. Thus different AONs can be designed to specifically hybridize to the mutated allele by targeting them to SNPs exclusively present in this allele. As there are many documented and common SNPs in NOTCH3, it is possible to use the same AON or AON-kit to treat patients with different mutations in the targeted exon(s), but with a common SNP in cis.

NOTCH3 Down-regulation

As an alternative to NOTCH3 cysteine quantity correction (protein modification) the invention uses exon-skipping to down-regulate the expression of the mutant protein. In this way reduction of NOTCH3 accumulation at the VSMC membrane will be accomplished, while maintaining sufficient wild-type NOTCH3 (wtNOTCH3) expression for normal VSMC homeostasis. In order to achieve this, AONs have been designed where the induced skip results in an out-of-frame transcript and non-sense mediated mRNA decay. The AONs are designed to be mutation or SNP specific, so that the wtNOTCH3 will not be targeted. This AON induced 'hemizygosity' of NOTCH3 expression does not compromise NOTCH3 function. Transgenic mouse lines hemizygously expressing either human wtNOTCH3 or human mutant NOTCH3 are viable and can rescue the structural arterial defects of Notch3−/− mice and the inventors have confirmed in a CADASIL patient an archetypal cysteine altering mutation on one allele and a deletion of NOTCH3 on the other allele. This patient has CADASIL, attributable to the missense mutation, but no other evident medical or vascular problems. Thus reduced NOTCH3 expression is compatible with life and normal vascular function. In this embodiment the AON is targeted to the mutation and/or an allele specific SNP that is not present on the normal allele.

CADASIL is a systemic arteriopathy i.e. all arteries of a certain caliber show mural changes typical for CADASIL. However, for unknown reasons, the small-to medium sized cerebral arteries carry the brunt of the pathology. It is these arteries and specifically the VSMCs that are targeted by the AONs. AONs can be injected intravenously or directly into the cerebrospinal fluid. The AONs used in the invention are preferably of 2'-O-methyl modified RNA (to prevent RNase H induced knockdown of RNA:RNA hybrids) with a phosphorothioate backbone, for improved stability. An added benefit of the phosphorothioate modification is that it improves uptake of AONs over the cell membrane. In addition, the modification leads to low affinity binding to serum proteins, which serve as carriers of the AONs in the bloodstream and prevent clearance of AON by the kidney. Thus the serum half life of the AONs is increased, which allows for better tissue distribution.

In mouse models of Duchenne muscular dystrophy, it has been shown that AONs can be delivered systemically after intravenous, subcutaneous and intraperitoneal injections. In addition, they are taken up in the smooth muscle cells of the epidermis (submitted manuscript and manuscript in press). Thus, AONs are taken up by VSMCs as well.

Local and systemic treatment with AONs of this chemistry at high doses (up to 600 mg/kg) for up to six months is tolerated well by patients in clinical trials for cancer, chronic immune diseases, atherosclerosis and Duchenne muscular dystrophy.

AONs designed against NOTCH3 specific sequences can lead to pre-mRNA skipping in such a way that an even number of 6 cysteine residues is re-established in a given EGFL domain, whilst maintaining an in-frame reading frame. This includes both mutation-specific and exon-specific AONs, as well as SNP-specific AONs. The aim is to design AONs targeted to the NOTCH3 mutation preferably to the hotspots of exons 3, 4 and 5, so that a maximum number of mutations can be targeted with each AON. AONs designed against NOTCH3 specific sequences can also be made such that pre-mRNA skipping results in an out-of-frame product and nonsense mediated mRNA decay is induced.

Figure 1:
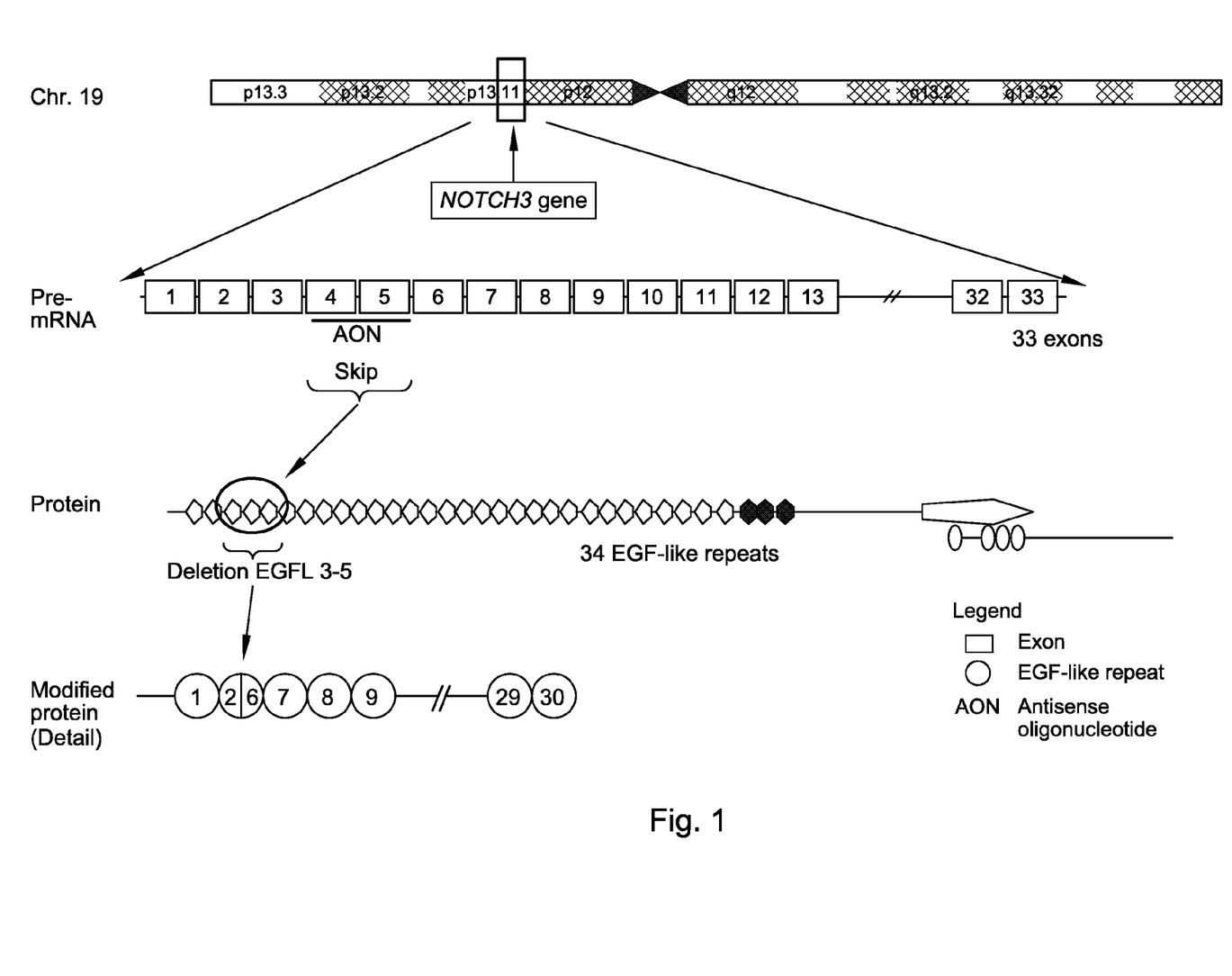
FIG. 1 illustrates how the skipping of exon 4 and exon 5 of the NOTCH3 gene on the short arm of chromosome 19 results in the exclusion of EGFL-repeats 3-5 and part of EGFL repeats 2 and 6. EGFL-repeats 2 and 6 form a fusion EGFL-repeat product with an equal number of cysteine residues. The modified NOTCH3 protein thus has 30 EGFL-repeats, wherein each EGFL-repeat has an equal number of cysteine residues.
Figure 2:
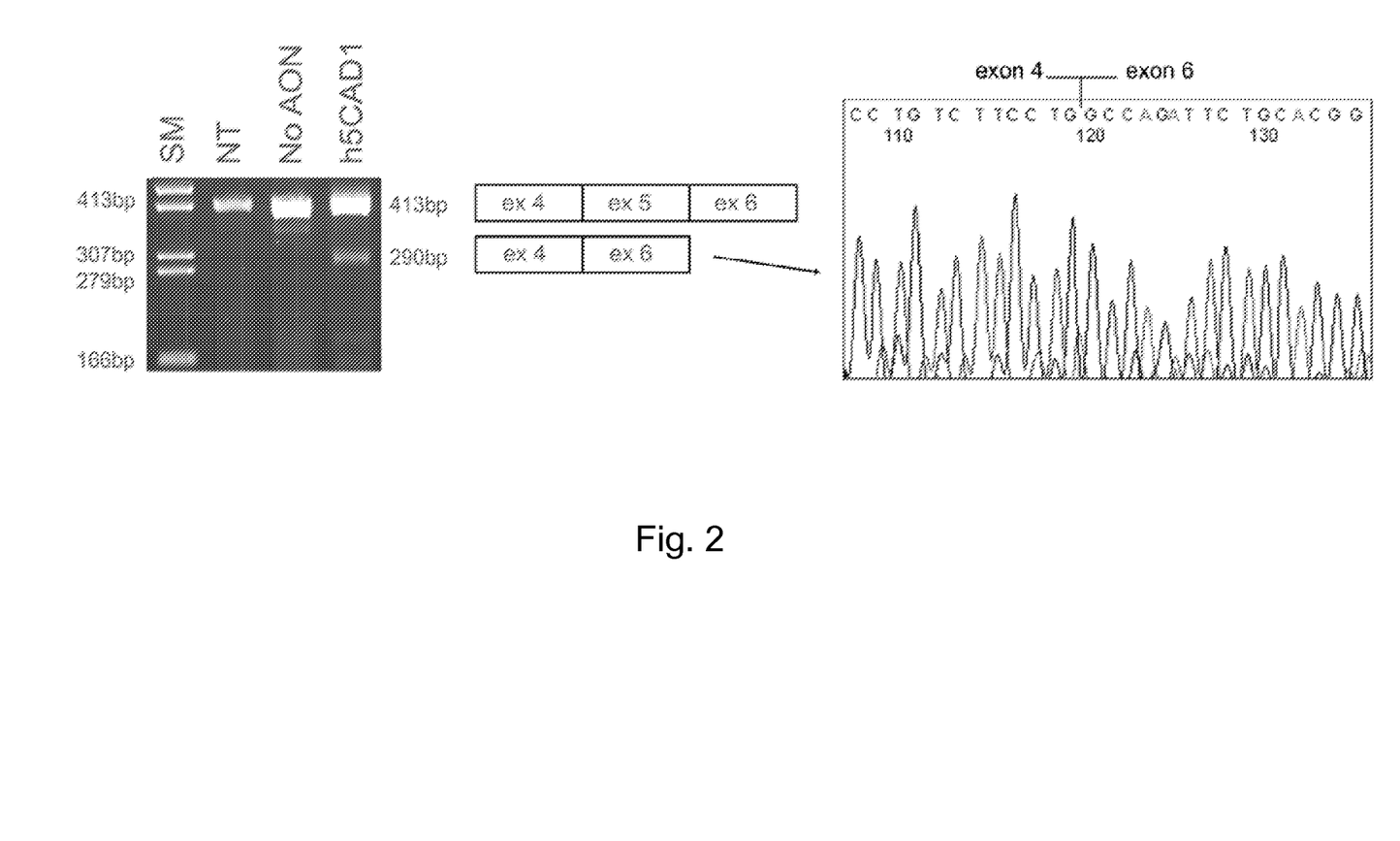

Legend to FIG. 2

RT-PCR and sequence analysis of NOTCH3 mRNA fragments of cell cultures treated with AON h5CAD1, focussing on the region encompassing exon 5. A shorter, novel transcript was observed (290 bp, lane 4) when compared to the untransfected cell cultures (lane 2) and cell cultures transfected without the AON (lane 3). Lane 1 contains a size marker (SM). Sequence analysis of the 290 bp fragment confirmed the precise skipping of exon 5.

Table 1 lists common mutations in exon 4 and exon 5 of the NOTCH3 gene, leading to CADASIL. This list is a selection of common mutations and is not a complete list of mutations found in exon 4 and exon 5 of the NOTCH3 gene. The left column shows the amino-acid substitution caused by the DNA mutation in the right hand column.

EXPERIMENTAL SECTION

Tissue culturing, transfection and RT-PCR analysis for AON h5CAD1. Notch3 expressing cell line HCC2429 was cultured as described by Dang et al. (1). For transfections the HCC2429 cells were grown to a confluency of 60-70% in 6 wells culture dishes. Transfections were performed in duplo with 900 pmol of AON h5CAD1 combined with 10 μl polyethylenimine (PEI, ExGen 500, MBI Fermentas) according to the manufacturer's instructions. Separate solutions of AON-PEI complexes were prepared for each AON. Transfection efficiencies were generally over 80% based on the presence of nuclear fluorescent signals using a fluorescently labeled AON as control. RNA was isolated 24 hours after transfection and RT-PCR analysis was performed as described previously (2). Successful skipping with AON h5CAD1 was confirmed by RT-PCR analysis with primers (4F: caacacacctggctccttc; 6R: gactgcagctctcacctgtc) in the exons 4 and 6 flanking the targeted exon 5. To control if exon 5 was skipped correctly, the PCR fragments of the expected size (290 bp) were isolated from an agarose gel and sequencing analysis was performed as described previously (3).

Cited References

1. Dang T P, et al. (2000). Chromosome 19 translocation, overexpression of Notch3, and human lung cancer. Journal of the National Cancer Institute 92(16): 1355-1357.
2. Aartsma-Rus A, Bremmer-Bout M, Janson A, Den Dunnen J, van Ommen G, and van Deutekom J. (2002). Targeted exon skipping as a potential gene correction therapy for Duchenne muscular dystrophy. Neuromuscul Disord 12: S71-S77.
3. van Deutekom JC, et al. (2001). Antisense-induced exon skipping restores dystrophin expression in DMD patient derived muscle cells. Hum Mol Genet 10: 1547-1554.

TABLE 1

Mutations in exon 4 and exon 5 of NOTCH3

Exon 4

| | | | |
|---|---|---|---|
| Arg133Cys; | 475 | CGC > | TGC |
| Cys134Trp; | 480 | TGC > | TGG |
| Arg141Cys; | 499 | CGC > | TGC |
| Cys144Phe; | 509 | TGC > | TTC |
| Arg153Cys; | 535 | CGC > | TGC |
| Cys162Trp; | 564 | TGC > | TGG |
| Arg182Cys; | 622 | CGC > | TGC |
| Tyr189Cys; | 644 | TAC > | TGC |
| Arg207Cys; | 697 | CGT > | TGT |
| Cys224Tyr; | 749 | TGT > | TAT |

Exon 5

| | | | |
|---|---|---|---|
| Cys233Trp; | 777 | TGT > | TGG |
| Tyr258Cys; | 851 | TAT > | TGT |

| AON specific for | AON sequence | AON name | % patients |
|---|---|---|---|
| Exon 4 | Agggugcacagggcaccgcggg (SEQ ID NO: 1) | h4CAD3 | ~70% |
| | Ugggcacaagggcugcugaggcagg (SEQ ID NO: 2) | h4CAD4 | |
| | aggaa gcguc caucg ggccc ca (SEQ ID NO: 3) | h4CAD5 | |
| | cggcagcugcggcccugguagcc (SEQ ID NO: 4) | h4CAD6 | |
| | gacacuggcagcggaaggagcc (SEQ ID NO: 5) | h4CAD7 | |
| | cguuacggcauggugaggguq (SEQ ID NO: 6) | h4CAD8 | |
| | ucgcuucggcagcugcggcc (SEQ ID NO: 7) | h4CAD9 | |
| | gguucucacauaguggcc (SEQ ID NO: 8) | h4CAD10 | |
| | cacucaccaggaagacagg (SEQ ID NO: 9) | h4CADSA | |
| | agcagucagggccuggaggga (SEQ ID NO: 10) | h4CADSD | |
| Exon 5 | Cccauugagacaucggugucc (SEQ ID NO: 11) | h5CAD1 | |
| | Uccacucaggagggcacug (SEQ ID NO: 12) | h5CAD2 | |
| | Guccacguucacuucacaauucugacc (SEQ ID NO: 13) | h5CAD3 | |

TABLE 1-continued

Mutations in exon 4 and exon 5 of NOTCH3

| | | |
|---|---|---|
| | ggcaguuauaggguguugacg (SEQ ID NO: 14) | h5CAD4 |
| | agacaucggugaccuggacagu (SEQ ID NO: 15) | h5CAD11 |
| | gacccucaaacccuagcagg (SEQ ID NO: 16) | h5CADSA |
| Arg141Cys (exon 4) | aggaa gcauc caucg ggccc ca (SEQ ID NO: 17) | h4CAD5M |
| Arg153Cys (exon 4) | cggcagcugcagcccugguagcc (SEQ ID NO: 18) | h4CAD6M |
| Arg207Cys (exon 4) | cguuacagcauggugagggug (SEQ ID NO: 19) | h4CAD8M |
| Arg182Cys (exon 4) | gacacuggcagcagaaggagcc (SEQ ID NO: 20) | h4CAD7M |
| Cys233Trp (exon 5) | guccacguucacuucccaauucugacc (SEQ ID NO: 21) | h5CAD3M |
| Tyr258Cys (exon 5) | ggcaguuacagguguugacg (SEQ ID NO: 22) | h5CAD4M |

The invention claimed is:

1. A method for producing an mRNA encoding a NOTCH3 protein having EGFL repeats with even numbers of cysteine residues from a pre-mRNA encoding a mutant NOTCH3 protein having an EGFL repeat with an uneven number of cysteine residues, comprising, providing a cell expressing said pre-mRNA with anti-sense oligonucleotides that are complementary to and hybridize with said pre-mRNA and wherein the anti-sense oligonucleotides are exon 4 and exon 5 internal oligonucleotides or directed toward the splice sites flanking the exons, and thereby inducing the exclusion of exon 4 and exon 5 from mRNA produced from said pre-mRNA, resulting in the cell producing an mRNA encoding a NOTCH3 protein having EGFL repeats with even numbers of cysteine residues;
wherein the produced mRNA comprises an exon 3-6 joining that is in frame and encodes a NOTCH3 protein in which the EGFL repeats all have an even number of cysteine residues, and
wherein the oligonucleotides comprise a chemical modification that renders a duplex formed by the antisense oligonucleotides and the target pre-mRNA resistant to RNAseH.

2. The method according to claim 1, wherein said EGFL-repeat with an uneven number of cysteines is encoded by exon 4 and/or exon 5.

3. The method according to claim 2, wherein said pre-mRNA encodes a NOTCH3 protein with a mutation at Arg133Cys, Cys134Trp, Arg141Cys, Cys144Phe, Arg153Cys, Cys162Trp, Arg182Cys, Tyr189Cys, Arg207Cys, Cys224Tyr, Arg207Cys, Cys224Tyr or a combination thereof.

4. The method according to claim 1, wherein said cell is a vascular smooth muscle cell (VSMC).

5. The method according to claim 1, wherein said antisense oligonucleotides comprise between 15-40 nucleotides specific for said NOTCH3 mRNA or pre-mRNA.

6. The method according to claim 1, wherein the duplex formed by the antisense oligonucleotides and the target pre-mRNA comprises 2'O-methyl phosphorothioate oligonucleotides, phosphorodiamidate morpholino oligomers (PMO) or 2'-O-methoxyethyl RNA with or without a phosphorothioate backbone.

* * * * *

SEQUENCE LISTING

<160> NUMBER OF SEQ ID NOS: 22

<210> SEQ ID NO 1
<211> LENGTH: 22
<212> TYPE: RNA
<213> ORGANISM: Artificial
<220> FEATURE:
<223> OTHER INFORMATION: AON exon 4

<400> SEQUENCE: 1
agggugcaca gggcaccgcg gg                                           22

<210> SEQ ID NO 2
<211> LENGTH: 25
<212> TYPE: DNA
<213> ORGANISM: Artificial
<220> FEATURE:
<223> OTHER INFORMATION: AON exon 4

<400> SEQUENCE: 2
ugggcacaag ggcugcugag gcagg                                        25

<210> SEQ ID NO 3
<211> LENGTH: 22
<212> TYPE: DNA
<213> ORGANISM: Artificial
<220> FEATURE:
<223> OTHER INFORMATION: AON exon 4

<400> SEQUENCE: 3
aggaagcguc caucgggccc ca                                           22

<210> SEQ ID NO 4
<211> LENGTH: 23
<212> TYPE: DNA
<213> ORGANISM: Artificial
<220> FEATURE:
<223> OTHER INFORMATION: AON exon 4

<400> SEQUENCE: 4
cggcagcugc ggcccuggua gcc                                          23

<210> SEQ ID NO 5
<211> LENGTH: 22
<212> TYPE: DNA
<213> ORGANISM: Artificial
<220> FEATURE:

```
<223> OTHER INFORMATION: AON exon 4

<400> SEQUENCE: 5
gacacuggca gcggaaggag cc                                              22

<210> SEQ ID NO 6
<211> LENGTH: 21
<212> TYPE: DNA
<213> ORGANISM: Artificial
<220> FEATURE:
<223> OTHER INFORMATION: AON exon 4

<400> SEQUENCE: 6
cguuacggca uggugagggu g                                               21

<210> SEQ ID NO 7
<211> LENGTH: 20
<212> TYPE: RNA
<213> ORGANISM: Artificial
<220> FEATURE:
<223> OTHER INFORMATION: AON exon 4

<400> SEQUENCE: 7
ucgcuucggc agcugcggcc                                                 20

<210> SEQ ID NO 8
<211> LENGTH: 18
<212> TYPE: RNA
<213> ORGANISM: Artificial
<220> FEATURE:
<223> OTHER INFORMATION: AON exon 4

<400> SEQUENCE: 8
gguucucaca uaguggcc                                                   18

<210> SEQ ID NO 9
<211> LENGTH: 19
<212> TYPE: RNA
<213> ORGANISM: Artificial
<220> FEATURE:
<223> OTHER INFORMATION: AON exon 4

<400> SEQUENCE: 9
cacucaccag gaagacagg                                                  19

<210> SEQ ID NO 10
<211> LENGTH: 21
<212> TYPE: RNA
<213> ORGANISM: Artificial
<220> FEATURE:
<223> OTHER INFORMATION: AON exon 4

<400> SEQUENCE: 10
agcagucagg gccuggaggg a                                               21

<210> SEQ ID NO 11
<211> LENGTH: 21
<212> TYPE: DNA
<213> ORGANISM: Artificial
<220> FEATURE:
<223> OTHER INFORMATION: AON exon 5

<400> SEQUENCE: 11
cccauugaga caucggugur c                                               21
```

```
<210> SEQ ID NO 12
<211> LENGTH: 19
<212> TYPE: DNA
<213> ORGANISM: Artificial
<220> FEATURE:
<223> OTHER INFORMATION: AON exon 5

<400> SEQUENCE: 12
uccacucagg agggcacug                                                  19

<210> SEQ ID NO 13
<211> LENGTH: 27
<212> TYPE: DNA
<213> ORGANISM: Artificial
<220> FEATURE:
<223> OTHER INFORMATION: AON exon 5

<400> SEQUENCE: 13
guccacguuc acuucacaau ucugacc                                         27

<210> SEQ ID NO 14
<211> LENGTH: 20
<212> TYPE: DNA
<213> ORGANISM: Artificial
<220> FEATURE:
<223> OTHER INFORMATION: AON exon 5

<400> SEQUENCE: 14
ggcaguuaua gguguugacg                                                 20

<210> SEQ ID NO 15
<211> LENGTH: 22
<212> TYPE: RNA
<213> ORGANISM: Artificial
<220> FEATURE:
<223> OTHER INFORMATION: AON exon 5

<400> SEQUENCE: 15
agacaucggu guccuggaca gu                                              22

<210> SEQ ID NO 16
<211> LENGTH: 20
<212> TYPE: RNA
<213> ORGANISM: Artificial
<220> FEATURE:
<223> OTHER INFORMATION: AON exon 5

<400> SEQUENCE: 16
gacccucaaa cccuagcagg                                                 20

<210> SEQ ID NO 17
<211> LENGTH: 22
<212> TYPE: DNA
<213> ORGANISM: Artificial
<220> FEATURE:
<223> OTHER INFORMATION: AON Arg141Cys (exon 4)

<400> SEQUENCE: 17
aggaagcauc caucgggccc ca                                              22

<210> SEQ ID NO 18
<211> LENGTH: 23
<212> TYPE: DNA
<213> ORGANISM: Artificial
<220> FEATURE:
<223> OTHER INFORMATION: AON Arg153Cys (exon 4)
```

```
<400> SEQUENCE: 18
cggcagcugc agcccuggua gcc                                          23

<210> SEQ ID NO 19
<211> LENGTH: 21
<212> TYPE: DNA
<213> ORGANISM: Artificial
<220> FEATURE:
<223> OTHER INFORMATION: AON Arg207Cys (exon 4)

<400> SEQUENCE: 19
cguuacagca uggugagggu g                                            21

<210> SEQ ID NO 20
<211> LENGTH: 22
<212> TYPE: DNA
<213> ORGANISM: Artificial
<220> FEATURE:
<223> OTHER INFORMATION: AON Arg182Cys (exon 4)

<400> SEQUENCE: 20
gacacuggca gcagaaggag cc                                           22

<210> SEQ ID NO 21
<211> LENGTH: 27
<212> TYPE: DNA
<213> ORGANISM: Artificial
<220> FEATURE:
<223> OTHER INFORMATION: AON Cys233Trp (exon 5)

<400> SEQUENCE: 21
guccacguuc acuucccaau ucugacc                                      27

<210> SEQ ID NO 22
<211> LENGTH: 20
<212> TYPE: DNA
<213> ORGANISM: Artificial
<220> FEATURE:
<223> OTHER INFORMATION: AON Tyr258Cys (exon 5)

<400> SEQUENCE: 22
ggcaguuaca gguguugacg                                              20
```